United States Patent [19]

Shimada

[11] Patent Number: 5,084,571
[45] Date of Patent: Jan. 28, 1992

[54] SUBSTITUTED THIAZOLE DYE COMPOUNDS

[75] Inventor: Yasuhiro Shimada, Minamiashigara, Japan

[73] Assignee: Fuji Photo Film Co., Ltd., Kanagawa, Japan

[21] Appl. No.: 423,221

[22] Filed: Oct. 18, 1989

[30] Foreign Application Priority Data

Oct. 20, 1988 [JP] Japan ................. 63-264764

[51] Int. Cl.$^5$ ................. C07D 277/20; C07D 417/00; C09B 57/00
[52] U.S. Cl. ................. 544/333; 546/280; 548/161; 548/181; 548/185; 548/192; 548/194; 548/195; 548/196
[58] Field of Search ............ 548/195, 194, 197, 196, 548/161, 181, 185, 192; 544/333; 546/280

[56] References Cited

U.S. PATENT DOCUMENTS

| | | | |
|---|---|---|---|
| 4,232,163 | 11/1980 | Cahoy | 548/195 |
| 4,239,894 | 12/1980 | Seybold et al. | 548/194 |
| 4,326,876 | 4/1982 | Aoyagi | 548/195 X |
| 4,395,544 | 7/1983 | Egli | 548/195 X |
| 4,788,284 | 11/1988 | Masukawa et al. | 544/139 |

FOREIGN PATENT DOCUMENTS

57-30759  2/1982  Japan ....................... 548/194

Primary Examiner—Mary C. Lee
Assistant Examiner—Fiona T. Powers
Attorney, Agent, or Firm—Birch, Stewart, Kolasch & Birch

[57] ABSTRACT

There are disclosed substituted thiazole dye compounds represented by the following Formula (I):

Formula (I)

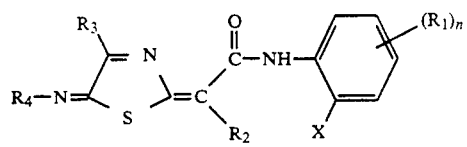

wherein $R_1$ represents a hydrogen atom or a group capable of substitution onto a benzene ring, n is an integer of 1 to 4, x represents a substitutent capable of forming a hydrogen bond with the hydrogen of —CONH—, $R_2$ represents an electron-attractive substituent, $R_3$ represents a group capable of substitution onto a thiazole ring, and $R_4$ represents an aromatic group or an unsaturated heterocyclic group that bonds to the nitrogen atom at a carbon atom having an unsaturated linkage.

The dye compounds provide a cyan color which is good in hues and possesses fastness to light and heat.

4 Claims, 1 Drawing Sheet

F I G.1

SUBSTITUTED THIAZOLE DYE COMPOUNDS

FIELD OF THE INVENTION

The present invention relates to a dye that can, for example, be used in forming a color image or can be used in filters.

BACKGROUND OF THE INVENTION

The properties required generally for dyes for forming images includes (1) stability or fastness to heat and light and (2) molecular extinction coefficient and hue. Conventionally, as cyan dyes for forming images, indoaniline dyes that are obtained from phenol compounds or naphthol compounds and p-phenylenediamines are commonly used. However, these indoaniline dyes do not necessarily satisfy items (1) and (2) above, and therefore further improvement was desired. To improve item (1) above, the use of compounds described in JP-B ("JP-B" means examined Japanese patent publication) No. 60423/1987 or JP-A ("JP-A" means unexamined published Japanese patent application) No. 30759/1982 can be mentioned. However, although these dyes were indeed fast to heat and light, the hue was not good, and the dyes had undesired subsidiary absorption in the blue region. To improve item (2) above, the use of compounds described in JP-A No. 113077/1988 can be mentioned. However, these dyes were quite poor in fastness to light and heat.

BRIEF SUMMARY OF THE INVENTION

Therefore, the object of the present invention is to provide a dye fast to heat and light, high in molecular extinction coefficient, and excellent in hue.

The above and other objects, features, and advantages of the invention will become apparent in the following description and drawings.

DETAILED DESCRIPTION OF THE INVENTION

The objects of the present invention have been attained by a dye compound represented by the following formula (I):

Formula (I)

wherein $R_1$ represents a hydrogen atom or a group capable of substitution on a benzene ring, n is an integer of 1 to 4, X represents a substituent capable of forming hydrogen bond with the hydrogen of —CONH—, $R_2$ represents an electron-attractive substituent. $R_3$ represents a group capable of substitution on a thiazole ring, and $R_4$ represents an aromatic group or an unsaturated heterocyclic group that bonds to the nitrogen atom at a carbon atom having an unsaturated linkage.

The compounds represented by formula (I) will now be described in detail.

Substituent $R_1$ represents, for example, a hydrogen atom, a halogen atom (e.g., chlorine and bromine), a linear or branched, straight-chain or cyclic aliphatic group which may be saturated or unsaturated, or may be substituted or unsubstituted (having preferably 1 to 30 carbon atoms, more preferably 1 to 15 carbon atoms, e.g., the following alkyl, alkenyl, or cycloalkyl, such as methyl, propyl, t-butyl, trifluoromethyl, tridecyl, 3-(2,4-di-t-amylphenoxy)propyl, 2-dodecyloxyethyl, 3-phenoxypropyl, 2-hexylsulfonylethyl, cyclopentyl, benzyl, ally, and propargyl), a heterocyclic group (e.g., preferably 5- to 7-membered ring containing O, N, or S as a hetero atom, such as 2-furyl, 2-thienyl, 2-pyrimidyl, and 2-benzothiazolyl), a cyano group, an alkoxy group (having preferably 1 to 30 carbon atoms, more preferably 1 to 15 carbon atoms, e.g., methoxy, ethoxy, 2-methoxyethoxy, 2-dodecyloxyethoxy, and 2-methanesulfonylethoxy), an aryloxy group (having preferably 6 to 30 carbon atoms, more preferably 6 to 10 carbon atoms, e.g., phenoxy, 2-methylphenoxy, and 4-t-butylphenoxy), a heterocyclic oxy group (e.g., preferably 5- to 7-membered ring containing O, N, or S as a hetero atom, such as 2-benzimidazolyloxy), an acyloxy group (having preferably 1 to 30 carbon atoms, more preferably 1 to 26 carbon atoms, e.g., acetoxy and hexadecanoyloxy), a carbamoyloxy group (having preferably 1 to 20 carbon atoms, more preferably 1 to 10 carbon atoms, e.g., N-ethylcarbamoyloxy), a sulfonyloxy group (having preferably 1 to 30 carbon atoms, more preferably 1 to 12 carbon atoms, e.g., dodecylsulfonyloxy), an acylamino group (having preferably 1 to 30 carbon atoms, more preferably 1 to 26 carbon atoms, e.g., acetamido, benzamido, tetradecanamido, α-(2,4-t-amylphenoxy)butyramido, 2,4-di-t-amylphenoxyacetamido, α-{4-(4-hydroxyphenylsulfonyl)phenoxy}-decanamido, and isopentadecanamido), an anilino group (having preferably 6 to 30 carbon atoms, more preferably 6 to 20 carbon atoms, e.g., phenylamino, 2-chloroanilino, 2-chloro-5-tetradecanamidoanilino, 2-chloro-5-dodecyloxycarbonylanilino, N-acetylanilino, and 2-chloro-5-{α-(2-t-butyl-4-hydroxyphenoxy)-dodecanamido}anilino), a ureido group (having preferably 1 to 10 carbon atoms, more preferably 1 to 6 carbon atoms, e.g., phenylureido, methylureido, and N,N-dibutylureido), a sulfamoylamino group (having preferably 1 to 20 carbon atoms, more preferably 1 to 12 carbon atoms, e.g., N,N-dipropylsulfamoylamino and N-methyl-N-decylsulfamoylamino), an alkylthio group (having preferably 1 to 30 carbon atoms, more preferably 1 to 15 carbon atoms, e.g., methylthio, octylthio, tetradecylthio, 2-phenoxyethylthio, 3-phenoxypropylthio, and 3-(4-t-butylphenoxy)propylthio), an arylthio group (having preferably 6 to 30 carbon atoms, more preferably 6 to 10 carbon atoms, e.g., phenylthio, 2-butoxy-5-t-octylphenylthio, 3-pentadecylphenylthio, 2-carboxyphenylthio, and 4-tetradecanamidophenylthio), a heterocyclic thio group (e.g., preferably 5- to 7-membered ring containing O, N, or S, as a hetero atom, such as 2-benzothiazolylthio), an alkoxycarbonylamino group (having preferably 2 to 31 carbon atoms, more preferably 2 to 16 carbon atoms, e.g., methoxycarbonylamino and tetradecyloxycarbonylamino), an aryloxycarbonylamino group (having preferably 7 to 31 carbon atoms, more preferably 7 to 11 carbon atoms, e.g., phenoxycarbonylamino and 2,4-di-tert-butylphenoxycarbonylamino), a sulfonamido group (having preferably 1 to 30 carbon atoms, more preferably 1 to 20 carbon atoms, e.g., methanesulfonamido, hexadecanesulfonamido, benzenesulfonamido, p-toluenesulfonamido, octadecanesulfonamido, and 2-methyloxy-5-t-butylbenzenesulfonamido), a carbamoyl group (having preferably 1 to 20 carbon atoms, more preferably 1 to 10 carbon atoms, e.g., N-ethylcarbamoyl, N,N-dibutylcarbomoyl, N-(2- dodecyloxyethyl)-carbamoyl, N-methyl-N-dodecylcarbamoyl, and N-{3-(2,4-di-tert-amylphenoxy)propyl}carbamoyl), an acyl group (having preferably 1 to 30 carbon atoms, more preferably 1 to 26 carbon atoms, e.g., acetyl, (2,4-di-tert-amylphenoxy)acetyl, and benzoyl), a sulfamoyl group (having preferably 1 to 30 carbon atoms, more preferably 1 to 20 carbon atoms, e.g., N-ethylsulfamoyl, N,N-dipropylsulfamoyl, N-(2-dodecyloxyethyl)sulfamoyl, N-ethyl-N-dodecylsulfamoyl and N,N-diethylsulfamoyl), a sulfonyl group (having preferably 1 to 30 carbon atoms, more preferably 1 to 20 carbon atoms, e.g., methanesulfonyl, octanesulfonyl, benzenesulfonyl, and toluenesulfonyl), a sulfinyl group (having preferably 1 to 30 carbon atoms, more preferably 1 to 20 carbon atoms, e.g., octanesulfinyl, dodecylsulfinyl, and phenylsulfinyl), an alkoxycarbonyl group (having preferably 2 to 31 carbon atoms, more preferably 2 to 16 carbon atoms, e.g., methoxycarbonyl, butyloxycarbonyl, dodecylcarbonyl, and octadecylcarbonyl), an aryloxycarbonyl group (having preferably 7 to 31 carbon atoms, more preferably 7 to 11 carbon atoms, e.g., phenyloxycarbonyl and 3-pentadecyloxycarbonyl), a carboxyl group or its salt, or a sulfone group or its salt. When n is 2 or over, $R_1$'s may be the same or different.

Substituent X is a group capable of forming a hydrogen bond with the hydrogen of —NHCO— in the ortho position of a phenyl group, for example, a halogen atom (e.g., chlorine, bromine, and fluorine), a fluorinated alkyl group having preferably 1 to 30 carbon atoms, more preferably 1 to 15 carbon atoms, an alkoxy group (having preferably 1 to 30 carbon atoms, more preferably 1 to 15 carbon atoms, e.g., methoxy, ethoxy, 2-methoxyethoxy, tetradecyloxy, 2-dodecyloxyethoxy, and 2-methanesulfonylethoxy), an aryloxy group (having preferably 6 to 30 carbon atoms, more preferably 6 to 10 carbon atoms, e.g., phenoxy, 2-methylphenoxy, and 4-t-butylphenoxy), a heterocyclic oxy group (e.g., preferably 5- to 7-membered ring containing O, N, or S as a hetero atom, such as 2-benzimidazolyloxy), an acyloxy group (having preferably 1 to 30 carbon atoms, more preferably 1 to 16 carbon atoms, e.g., acetoxy and hexadecanoyloxy), an acylamino group (having preferably 1 to 30 carbon atoms, more preferably 1 to 16 carbon atoms, e.g., acetamido and benzamido, an acyl group (e.g., acetyl and benzoyl), an alkoxycarbonyl group (having preferably 2 to 31 carbon atoms, more preferably 2 to 16 carbon atoms, e.g., methoxycarbonyl, dodecylcarbonyl, and octadecylcarbonyl), an alkylthio group (having preferably 1 to 30 carbon atoms, more preferably 1 to 15 carbon atoms, e.g., methylthio, octylthio, and tetradecylthio), an arylthio group (having preferably 6 to 30 carbon atoms, more preferably 6 to 10 carbon atoms, e.g., phenylthio and 2-carboxyphenylthio), or a heterocyclic thio group (e.g., 2-benzothiazolylthio). Of these substituents, preferable substituents are halogen atoms, fluorinated alkyl group, alkoxy groups, and acyl groups.

In formula (I), more particularly $R_2$ represents a substituent the value of the Hammett substituent constant $\sigma_p$ of which is greater than 0, preferably the $\sigma_p$ is 0.3 to 0.9, and more preferably 0.5 to 0.9. $R_2$ represents, for example, a cyano group, a carbamoyl group (having preferably 1 to 30 carbon atoms, more preferably 1 to 16 carbon atoms, e.g., N-phenylcarbamoyl, N-(2-chloro-5-tetradecyloxycarbonylphenyl)carbamoyl, N,N-diethylcarbamoyl, N-(2,4-dichlorophenyl)carbamoyl, and N-(2-chloro-5-hexadecanesulfonamidophenyl)carbamoyl), an alkoxycarbonyl group (having preferably 2 to 31 carbon atoms, more preferably 2 to 16 carbon atoms ,e.g., ethoxycarbonyl, butoxycarbonyl, dodecyloxycarbonyl, and 2-ethylhexyloxycarbonyl), an aryloxycarbonyl group (having preferably 7 to 31 carbon atoms, more preferably 7 to 11 carbon atoms, e.g., phenoxycarbonyl and 1-naphthyloxycarbonyl), an acyl group (having preferably 1 to 30 carbon atoms, more preferably 1 to 26 carbon atoms, e.g., benzoyl, 4-chlorobenzoyl, and 2,4-dichlorobenzoyl), a sulfonyl group (having preferably 1 to 30 carbon atoms, more preferably 1 to 20 carbon atoms, e.g., methanesulfonyl, dodecanesulfonyl, benzenesulfonyl, and 2-butoxy-5-t-octylphenylsulfonyl), a sulfamoyl group (having preferably 1 to 30 carbon atoms, more preferably 1 to 20 carbon atoms, e.g., N-butylsulfamoyl, N-phenylsulfamoyl, and N,N-diethylsulfamoyl), a nitro group, a fluorinated alkyl group (having preferably 1 to 30 carbon atoms, more preferably 1 to 15 carbon atoms, e.g., trifluoromethyl and heptafluoropropyl), a sulfinyl group (having preferably 1 to 30 carbon atoms, more preferably 1 to 20 carbon atoms, e.g., methanesulfinyl, benzenesulfinyl, and naphthalenesulfinyl), an aromatic group (having preferably 6 to 30 carbon atoms, more preferably 6 to 10 carbon atoms, e.g., phenyl, 4-chlorophenyl, and 4-acetamidophenyl), a carboxyl group or its salt, or a sulfone group or its salt.

In formula (I), $R_3$ represents, for example, a hydrogen atom, a halogen atom (e.g., fluorine, chlorine, and bromine), a linear or branched aliphatic group (e.g., methyl, propyl, t-butyl, and dodecyl), an alkoxy group (having preferably 1 to 30 carbon atoms, more preferably 1 to 10 carbon atoms, e.g., methoxy, ethoxy, and 2-methoxyethoxy), an aryloxy group (having preferably 6 to 30 carbon atoms, more preferably 6 to 15 carbon atoms, e.g., phenoxy and 2-methylphenoxy), an amino group, a ureido group (having preferably 1 to 30 carbon atoms, more preferably 1 to 10 carbon atoms, e.g., phenylureido and methylureido), a carbamoyloxy group (having preferably 1 to 30 carbon atoms, more preferably 1 to 20 carbon atoms, e.g., N-ethylcarbamoyloxy), an aryl group (having preferably 6 to 30 carbon atoms, more preferably 6 to 15 carbon atoms, e.g., phenyl, 4-tetradecanamidophenyl, 4-bromophenyl, 4-methylthiophenyl, and 4-methoxyphenyl), an acylamino group (having preferably 1 to 30 carbon atoms, more preferably 1 to 15 carbon atoms, e.g., heptafluoropropylamido, acetamido, benzamido, and tetradecanamido) a carboxyl group or its salt, or a sulfone group or its salt.

In formula (I), if $R_4$ represents an aromatic group, the number of the carbon atoms of the aromatic group is 6 to 10, and preferably $R_4$ represents a substituted or unsubstituted phenyl group. When $R_4$ represents a heterocyclic group, the heterocyclic group is a 5- to 7-membered unsaturated heterocyclic ring whose hetero atom is selected from a nitrogen atom, an oxygen atom, or a sulfur atom. As a typical heterocyclic group, a 2-pyridyl group, a 2-benzothiazolyl group, or a 2-pyrolyl group can be mentioned.

If the aromatic group and the heterocyclic group for $R_4$ have a substituent, examples of the substituent include those mentioned for $R_1$.

Specific examples of dye compounds of the present invention are given below, but the present invention is not limited to them.

(1)

(2)

(3)

(4)

(5)

-continued (6)

(7)

(8)

(9)

(10)

(11)

-continued (12)

(13)

(14)

(15)

(16)

-continued

(17)

(18)

(19)

(20)

(21)

-continued

(22)

(23)

(24)

(25)

(26)

(27)

-continued (28)

(29)

(30)

(31)

The dye represented by formula (I) is obtained by coupling of a coupler represented by formula (II), given below, preferably with an oxidized product of an aromatic primary amine represented by formula (III), given below.

Formula (II)

wherein $R_0$ represents a hydrogen atom or a group capable of being released upon coupling and $R_1$, $R_2$, $R_3$, and X have the same meanings as those defined in formula (I). The group capable of being released upon coupling for $R_0$ represents, for example, a halogen atom (e.g., chlorine and bromine), an alkoxy group (having preferably 1 to 10 carbon atoms, more preferably 1 to 5 carbon atoms, e.g., methoxy, ethoxy), an aryloxy group (having preferably 6 to 20 carbon atoms, more preferably 6 to 10 carbon atoms, e.g., phenoxy).

Formula (III)

wherein $R_{11}$ and $R_{12}$, which may be the same or different, each represent a hydrogen atom or an optionally substituted alkyl group, $R_{13}$ represents a hydrogen atom, a halogen atom, or an optionally substituted alkyl group, n' represents the number of the substituent $R_{13}$'s, and is 1 or 2, and when n is 2, the $R_{13}$'s may be the same or different.

When the amine represented by formula (III) is used in the form of a salt with an inorganic acid (mineral acid) or an organic acid, oxidation with air can be easily prevented and the dissolution velocity can be improved.

Preferably $R_{11}$ and $R_{12}$ of formula (III) each represent a hydrogen atom, an alkyl group, or a substituted alkyl group, such as hydroxyalkyl, alkoxyalkyl, alkoxyalkoxyalkyl, or alkylsulfonamidoalkyl.

Examples of the alkyl group and the alkoxy group of the phenylene diamine derivative (III), and examples of the alkyl of the substituted alkyl group and the alkyl of the alkoxy group of the phenylene diamine derivative (III), are a lower alkyl group having 1 to 4 carbon atoms, such as methyl, ethyl, n-propyl, iso-propyl, n-butyl, iso-butyl, sec-butyl, and t-butyl, a higher alkyl group having 5 to 18 carbon atoms, such as n-amyl, dl-2-methyl-1-butyl, iso-amyl, sec-amyl, t-amyl, n-hexyl, methylamyl, 2-ethylbutyl, n-heptyl, 2-heptyl, 3-heptyl, n-octyl, 2-octyl, 2-ethylhexyl, n-dodecyl, n-octadecyl, and cyclohexyl, including linear, branched, and cyclic alkyl groups. Halogen examples include chlorine, bromine, and iodine.

The primary amines (III) used for synthesis of the dyes of the present invention are preferably ortho or para phenylenediamines, more preferably para phenylene diamines.

Specific examples are:
those having an N-alkyl group, for example
  D1) 4-amino-N-ethylaniline,
  D2) 4-amino-N,N-diethylaniline, and
  D3) 4-amino-3-methyl-N,N-diethylaniline,
those having an N-hydroxyalkyl group, for example
  D4) 4-amino-N-ethyl-N-($\beta$-hydroxyethyl)aniline and
  D5) 4-amino-3-methyl-N-ethyl-N-($\beta$-hydroxyethylaniline),
those having an N-alkoxyalkyl group, for example
  D6) 4-amino-3-methyl-N-ethyl-($\beta$-methoxyethyl)aniline,
  D7) 4-amino-3-methyl-N-ethyl-N-methoxybutylaniline,
  D8) 4-amino-3-methyl-N-ethyl-N-($\beta$-ethoxyethyl)aniline,
  D9) 4-amino-3-propyl-N-ethyl-N-($\beta$-methoxyethyl)aniline,
  D10) 4-amino-3-propyl-N-ethyl-N-($\beta$-ethoxyethyl)aniline,
  D11) 4-amino-3-methoxy-N-ethyl-N-($\beta$-methoxyethyl)-aniline, and
  D12) 4-amino-3-methyl-N-ethyl-N-($\beta$-butoxyethyl)aniline, those having an N-alkoxyalkoxyalkyl group, for example
  D13) 4-amino-3-methyl-N-ethyl-N-($\beta$-($\beta$-methoxyethoxy)-ethyl)aniline,
  D14) 4-amino-3-methyl-N-ethyl-N-($\beta$-($\beta$-ethoxyethoxy)-ethyl)aniline,
  D15) 4-amino-3-methyl-N-ethyl-N-($\beta$-($\beta$-butoxyethoxy)-ethyl)aniline,
  D16) 4-amino-3-methyl-N-methyl-N-($\beta$-($\beta$-methoxyethoxy)-ethyl)aniline,
  D17) 4-amino-N-ethyl-N-($\beta$-($\beta$-methoxyethoxy)ethyl)-aniline, and
  D18) 4-amino-N-ethyl-N-($\beta$-($\beta$-ethoxyethoxy)ethyl)aniline,
and those having an N-alkylsulfonamidoalkyl group, for example
  D19) 4-amino-N-ethyl-N-($\beta$-methylsulfonamidoethyl)aniline,
  D20) 4-amino-3-methyl-N-ethyl-N-($\beta$-methylsulfonamidoethyl)-aniline,
  D21) 4-amino-3-chloro-N-ethyl-N-($\beta$-methylsulfonamidoethyl)aniline, and
  D22) 4-amino-N-ethyl-($\beta$-methylsulfonamidoethyl)-3,5-xylidine.

Examples of their salts are inorganic acid salts of the above phenylenediamine derivatives, such as hydrohalides, for example hydrochlorides, hydrobromides, and hydroiodides, sulfates, nitrates, phosphates, and carbonates, and organic acid salts of the above phenylenediamine derivatives, such as aliphatic carboxylates, for example formates and acetates, aromatic carboxylates, for example benzoates, naphthalene-$\beta$-carboxylates, and naphthalene-$\beta$-carboxylates, and aliphatic sulfonates, for example methanesulfonates, naphthalene-$\alpha$-sulfonates, naphthalene-$\beta$-sulfonates, and p-toluenesulfonates. It is preferable that these salts are selected suitably according to the production conditions of the dye, and, for example, if the compound is used as a photographic color-forming developing agent, the dye is preferably one that will not affect the photographic quality. Therefore, generally the primary amines (III) are used in the form of inorganic acid salts, such as sulfates, or aromatic sulfonates, such as p-toluenesulfonates or the like.

The dyes of the present invention are particularly useful as photographic cyan dye that can be obtained, for example, by coupling a coupler represented by formula (II) mentioned above, as cyan coupler used in silver halide color photographic materials, with an oxydized product of the developing agent represented by formula (III) mentioned above that can be obtained after oxidation of an exposed silver halide.

The dyes of the present invention can also be used as a disperse dye in filters for photography and filters for solid state imaging tubes, color liquid crystal television sets, or the like. The dyes of the present invention are also useful as cyan dyes for images, for example, in printing, color electrophotography, ink jet printing systems, and heat sensitive copying processes described, for example, in JP-A Nos. 149048/1983, 18169/1983, 205798/1983, and 219086/1983.

The dyes of the present invention are quite good in hue as cyan dye for the above application, and quite fast to light and heat, and they have high molecular extinction coefficients.

The present invention will now be described in more detail with reference to Examples. For the dyes obtained in the Examples, molecular extinction coefficients are shown in Table 1 below.

EXAMPLE 1

Synthesis of Exemplified Compound (1)

Exemplified Compound (1) was synthesized by the following route.

1.0 g of Compound (50) was dissolved in 10 ml of anhydrous tetrahydrofuran, and 6.8 ml of a hexane containing (n)-((n)-butyllithium)butyllithium (1.55 M) was added dropwise thereto over 5 min under a nitrogen atmosphere with the reaction temperature kept at $-78°$ C. After the addition the mixture was stirred for 30 min, and then 1.7 g of Compound (51) dissolved in 5 ml of anhydrous tetrahydrofuran was added dropwise over 10 min. After the completion of the reaction, 50 ml of ethyl acetate layer was added, followed by washing with water. The ethyl acetate layer was dried over magnesium sulfate, then the ethyl acetate layer was distilled off under reduced pressure, and the residue was recrystallized from 10 ml of acetone and 10 ml of tetrahydrofuran. The crystals were filtered off, to produce 1.2 g (yield 27.8 of an intermediate product (52). 450 mg of the obtained product (52) was dissolved in 10 ml of ethanol, and 652 mg of sodium carbonate dissolved in 5 ml of water was added thereto. Further, 640 mg of Compound (53) and 670 mg of ammonium persulfate were added thereto, and the mixture was stirred for 30 min at room temperature. The separated crystals were washed well with water and then filtered off, to yield 260 mg of the desired Exemplified Compound (1) (yield 43.6%).

Elementary analysis:

|  | H | C | N | Cl |
|---|---|---|---|---|
| Calculated (%) | 4.20 | 55.66 | 10.82 | 21.90 |

-continued

|  | H | C | N | Cl |
|---|---|---|---|---|
| Found (%) | 4.12 | 55.48 | 10.75 | 21.77 |

EXAMPLE 2

Synthesis of Exemplified Compound (2)

Exemplified Compound (2) was synthesized by the following route.

3.0 g of Compound (54) and 7.1 g of Compound (55) were dissolved in 50 ml of dimethylformamide, then 7.1 ml of triethylamine was added thereto and the mixture was stirred for 20 min at 25° C. After completion of the reaction, acetic acid was added to neutralize the reaction mixture. The separated crystals were filtered off, to obtain 4.4 g of an intermediate product (56) (yield 54.7%).

1.0 g of the thus-obtained product (56) and 1.4 g of Compound (57) were reacted similarly to Example (1), to yield 1.1 g of the desired Exemplified Compound (2) (in a yield of 75.5%).

Elemental analysis:

|  | H | C | N | Cl |
|---|---|---|---|---|
| Calculated (%) | 6.66 | 59.17 | 10.89 | 4.60 |
| Found (%) | 6.63 | 59.09 | 10.92 | 4.50 |

EXAMPLE 3

Synthesis of Exemplified Compound (3)

Similarly to Example (2), Exemplified Compound (3) was synthesized by the following route.

0.5 g of Compound (54), 2.0 g of Compound (58), and 1.1 ml of triethylamine were dissolved in 50 ml of dimethylformamide, and they were reacted similarly to Example 2 to produce 1.2 g of an intermediate product (59) (yield 32.7%).

Further, 1.2 g of Compound (59) and 0.74 g of Compound (54) were reacted in ethanol similarly to Example (1), to yield 0.88 g of the desired E exemplified Compound (3) (yield 59.9%).

Elementary analysis:

|  | H | C | N | Cl |
|---|---|---|---|---|
| Calculated (%) | 7.50 | 64.98 | 6.77 | 6.85 |
| Found (%) | 7.39 | 64.69 | 6.68 | 6.83 |

EXAMPLE 4

Synthesis of Exemplified Compound (8)

Exemplified Compound (8) was synthesized by the following route.

3.0 g of Compound (60) and 3.7 g of Compound (61) were mixed and reacted at 120° to 130° C. for 2 hours with stirring. After completion of the reaction, while it was hot, 50 ml of ethyl acetate was added and the mixture was stirred until the temperature reached room temperature. The separated crystals were filtered off, to obtain 4.8 g of Compound (62) (yield 76.9%).

2.0 of Compound (62) was heated together with 1.0 g Compound (63) and 0.5 g of glacial acetic acid in ethanol under reflux. After completion of the reaction, 100 ml of ethyl acetate was added and the ethyl acetate layer was washed well with water. After the ethyl acetate layer was dried over magnesium sulfate, the ethyl acetate was distilled off under reduced pressure, then 10 ml of acetone and 10 ml of ethanol were added to the residue to effect recrystallization. The separated crystals filtered off to yield 1.7 g of the desired Exemplified Compound (8) (yield 57.8%).

Elementary analysis:

|  | H | C | N | Cl |
|---|---|---|---|---|
| Calculated (%) | 6.41 | 61.97 | 10.08 | 4.25 |
| Found (%) | 6.45 | 62.03 | 10.12 | 4.20 |

EXAMPLE 5

Synthesis of Exemplified Compound (16)

Exemplified Compound (16) was synthesized by the following route.

(64) (65)

(66)

(67)

(53) ⟶ (16)

10.0 g of Compound (64), 32.3 g of Compound (65), and 41.8 ml of triethylamine were dissolved in 100 ml of dimethylformamide, and the mixture was stirred for 24 hours at room temperature. After completion of the reaction 20 ml of ethyl acetate was slowly added dropwise, to allow the crystals to separate out. The crystals were filtered off to obtain 21.5 g of Compound (66) (yield 55.8%).

10.0 g of Compound (66) was dissolved in 100 ml of acetonitrile, and 9.0 g of Compound (67) was added slowly dropwise. After the addition the separated crystals were filtered off, to obtain 15.5 g of Compound (68) (yield 87.0%).

1.0 g of the thus-obtained Compound (68) and 0.44 g of Compound (53) were reacted in ethanol similarly to Example 1, to obtain 0.8 g of the desired Exemplified Compound (16) (yield 66.5%).

Elementary analysis:

|  | H | C | N | Cl |
|---|---|---|---|---|
| Calculated (%) | 6.67 | 67.11 | 9.58 | 8.08 |
| Found (%) | 6.52 | 67.02 | 9.49 | 8.02 |

EXAMPLE 6

Figure 1:
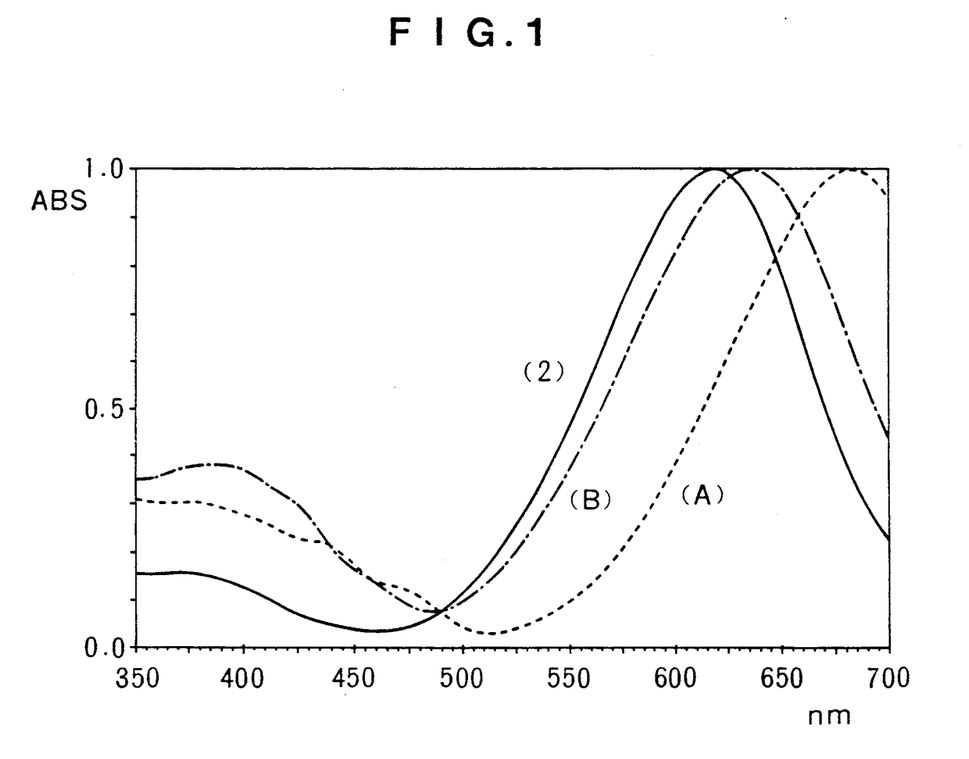
FIG. 1 is a graph showing the absorption spectrum of a dye compound of the present invention in comparison with the absorption spectrum of a prior dye.

With respect to Exemplified Compound (2) of the present invention, the absorption spectrum of the visible light region obtained in ethyl acetate solvent is shown in FIG. 1. The absorption spectra of Compound (A) and Compound (B) as comparative compounds are also shown.

Comparative Compound (A)

Comparative Compound (B)

With respect to the above-mentioned Exemplified Compounds typical of the present invention, the results of the measured molecular extinction coefficients (ε) are shown in Table 1.

TABLE 1

| Dye | ε (l·mol$^{-1}$·cm$^{-1}$) |
|---|---|
| Exemplified Compound (1) | 4.0 × 10$^4$ |
| Exemplified Compound (2) | 4.2 × 10$^4$ |
| Exemplified Compound (3) | 4.1 × 10$^4$ |
| Exemplified Compound (8) | 4.2 × 10$^4$ |
| Exemplified Compound (16) | 4.4 × 10$^4$ |
| Exemplified Compound (19) | 4.3 × 10$^4$ |
| Exemplified Compound (24) | 4.0 × 10$^4$ |
| Comparative Compound (C) | 2.7 × 10$^4$ |

TABLE 1-continued

| Dye | ε (l·mol⁻¹·cm⁻¹) |
|---|---|
| Comparative Compound (D) | 2.4 × 10⁴ |

Comparative Compound (C)

Comparative Compound (D)

Next, the fastnesses to light and heat of typical compounds among the above-mentioned Exemplified Compounds of the present invention were measured. The results are shown in Table 2, in comparison with those for the following comparative compounds (E), (F), and (G).

TABLE 2

Comparative compound (E)

Comparative compound (F)

Comparative compound (G)

TABLE 2-continued

Compound described in JP-A No. 113077/1988

| Dye | Fastness to Heat (%) | Fastness to Light (%) |
|---|---|---|
| Exemplified Compound (1) | 98 | 88 |
| Exemplified Compound (2) | 100 | 85 |
| Exemplified Compound (3) | 97 | 90 |
| Exemplified Compound (8) | 100 | 85 |
| Exemplified Compound (16) | 99 | 88 |
| Comparative compound (E) | 95 | 71 |
| Comparative compound (F) | 85 | 85 |
| Comparative compound (G) | <20 | 15 |

The fastness to heat is a ratio of residual dye density after being kept for 8 days at 100° C. to the initial density, and the fastness to light is a ratio of residual dye density after being irradiated by a Xenon lamp (85,000 Lux) for 6 days to the initial density.

As is apparent from the results in Table 2, the dye of the present invention is fast to both heat and light differing from phenol or naphthol dyes (E), (F), and (G).

As described above, the dyes of the present invention are low in subsidiary absorption in the blue region, and they have high molecular extinction coefficients compared to conventional phenol cyan dyes. This means that, for example, when the dyes of the present invention are used as cyan dye in forming images, the amount of the dye may be small to attain a certain density, and it is indicated that the lower subsidiary adsorption in the blue region is very advantageous in view of the color reproduction.

Further, these Exemplified Compounds of the present invention were good at fastness to heat and light.

Having described our invention as related to the embodiment, it is our intention that the invention be not limited by any of the details of the description, unless otherwise specified, but rather be construed broadly within its spirit and scope as set out in the accompanying claims.

What we claim is:

1. A dye compound represented by the following Formula (I):

$$\begin{array}{c}R_3\\R_4-N\end{array}\!\!=\!\!\begin{array}{c}N\\S\end{array}\!\!=\!\!\begin{array}{c}\phantom{x}\\C\\R_2\end{array}\!\!-\!\!\begin{array}{c}O\\\|\\C\!-\!NH\!-\!\end{array}\!\!\begin{array}{c}\phantom{x}\\\phantom{x}\\X\end{array}\!\!(R_1)_n$$

wherein,
n is an integer of 1 to 4, and when n is 2–4, the $R_1$'s may be the same or different;
$R_1$ in Formula (I) is selected from the group consisting of halogen, a linear or branched, straight-chain or cyclic, saturated or unsaturated, substituted or unsubstituted $C_{1-30}$ aliphatic, a heterocyclic selected from the group consisting of 2-furyl, 2-thienyl, 2-pyrimidyl and 2-benzothiazolyl; cyano, $C_{1-30}$ alkoxy, substituted or unsubstituted phenoxy wherein the phenyl moiety thereof may be substituted by methyl or t-butyl; heterocyclic-oxy wherein the heterocyclic moiety is 2-benzimidazolyl; $C_{2-30}$ carbacyloxy, $C_{2-30}$ carbamoyloxy, $C_{1-30}$ sulfonyloxy, $C_{2-30}$ carbacylamino; anilino, which may be substituted by phenyl, chloro, tetradecanamido, dopdecyloxycarbonyl, acetyl or α-(2-t-butyl-4hydroxyphenoxy)dodecanamido; $C_{1-10}$ ureido, $C_{1-20}$ sulfamoylamino, $C_{1-30}$ alkylthio, a substituted or unsubstituted phenylthio wherein the phenyl moiety thereof may be substituted by butoxy, oxtyl or 3-pentadecyl; heterocyclic-thio wherein the heterocyclic moiety is 2-benzothiazolyl; $C_{2-31}$ alkoxycarbonylamino, substituted or unsubstituted phenoxycarbonylamino wherein the phenyl moiety thereof may be substituted by t-butyl; $C_{1-30}$ sulfonamido, $C_{2-20}$ carbamoyl, $C_{2-30}$ carbacyl, $C_{1-30}$ sulfamoyl, $C_{1-30}$ sulfonyl, $C_{1-30}$ sulfinyl, $C_{2-31}$ alkoxycarbonyl, substituted or unsubstituted phenoxycarbonyl wherein the phenyl moiety thereof may be substituted by 3-pentadecyl; carboxyl or a salt thereof, and sulfone or a salt thereof;

X in Formula (I) represents a substituent capable of forming a hydrogen bond with the hydrogen of —CONH— and is selected from the group consisting of halogen, fluorinated $C_{1-30}$ alkyl, $C_{1-30}$ alkoxy, substituted or unsubstituted phenoxy wherein the phenyl moiety thereof may be substituted methyl or t-butyl; heterocyclic-oxy wherein the heterocyclic moiety is 2-benzimidazolyl; $C_{2-30}$ carbacyloxy, $C_{2-30}$ carbacylamino, acetyl, benzoyl, $C_{2-31}$ alkoxycarbonyl, $C_{1-30}$ alkylthio, substituted or unsubstituted phenylthio wherein the phenyl moiety thereof may be substituted by carboxy; and 2-benzothiazoluylthio;

$R_2$ in Formula (I) is selected from the group consisting of cyano, $C_{1-30}$ carbamoyl, $C_{2-31}$ alkoxycarbonyl, phenoxycarbonyl, 1-naphthyloxycarbonyl, $C_{2-30}$ carbacyl, $C_{1-30}$ sulfonyl, $C_{1-30}$ sulfamoyl, nitro, fluorinated $C_{1-30}$ alkyl, $C_{1-30}$ sulfinyl, substituted or unsubstituted phenyl wherein phenyl moiety may be substituted by chloro or acetamido; carboxyl or a salt thereof, and sulfone or a salt thereof;

$R_3$ in Formula (I) is selected from the group consisting of hydrogen, halogen, $C_{1-12}$ alkyl, $C_{1-30}$ alkoxy, substituted or unsubstituted phenoxy wherein the phenyl moiety thereof may be substituted by methyl; amino, $C_{1-30}$ ureido, $C_{2-30}$ carbamoyloxy, substituted or unsubstituted phenyl wherein phenyl moiety may be substituted by bromo, methyl or methoxy; $C_{2-30}$ carbacylamino, carboxyl or a salt thereof, and sulfone or a salt thereof; and $R_4$ in Formula (I) is phenyl which is unsubstituted or substituted by methyl or t-butyl, or a heterocyclic moiety selected from the group consisting of 2-pyridyl, 2-benzothiazolyl and 2-pyrole.

2. A dye compound represented by the following Formula (I):

Formula (I)

wherein, n is an integer of 1 to 4, and when n is 2–4, the $RF_1$'s may be the same or different;

$R_1$ in Formula (I) is selected from the group consisting of $C_{1-15}$ alkyl, $C_{2-15}$ alkenyl, $C_{3-15}$ cycloalkyl, 2-furyl, 2-thienyl, 2-pyrimidyl, 2-benzothiazolyl, cyano, $C_{1-15}$ alkoxy, phenoxy, 2-methylphenoxy, 4-t-butylphenoxy, benzimidazolyloxy, $C_{2-26}$ carbacyloxy, $C_{2-10}$ carbamoyloxy, $C_{1-12}$ sulfonyloxy, $C_{2-26}$ carbacylamino, phenylamino, 2-chloroanilino, 2-chloro-5tetradecanamidoanilino, 2-chloro-5dodecyloxycarbonylanilino, N-acetylanilino, 2-chloro-5-anilino, $C_{1-16}$ ureido, $C_{1-12}$ sulfamoylamino, $C_{1-15}$ alkylthio, phenylthio, 2-butoxy-5t-octylphenylthio, 3-pentadecylphenylthio, 2-carboxyphenylthio, 4-tetraconamidophenylthio, 2-benzothiazolylthio, $C_{2-16}$ alkoxycarbonylamino, phenoxycarbonylamino, 2,4-tert-butylphenoxycarbonylamino, $C_{1-20}$ sulfonamido, $C_{2-10}$ carbamoyl, $C_{2-26}$ carbacyl, $C_{1-20}$ sulfamoyl, $C_{1-20}$ sulfonyl, $C_{1-20}$ sulfinyl, $C_{2-16}$ alkoxycarbonyl, phenoxycarbonyl, 3-pentadecyloxycarbonyl, carboxyl or a salt thereof, and sulfone or a salt thereof;

X in Formula (I) represents a substituent capable of forming a hydrogen bond with the hydrogen of —CONH— and is selected from the group consisting of halogen, fluorinated $C_{1-15}$ alkyl, $C_{1-15}$ alkoxy, phenoxy, 2-methylphenoxy, 4-t-butylphenoxy, 2-benzimidazolyloxy, $C_{2-16}$ carbacyloxy, $C_{2-16}$ carbacylamino, acetyl, benzoyl, $C_{2-16}$ alkoxycarbonyl, $C_{1-15}$ alkylthio, phenylthio, 2-carboxyphenylthio, and 2-benzothiazolylthio;

$R_2$ in Formula (I) is selected from the group consisting of cyano, $C_{2-16}$ carbamoyl, $C_{2-16}$ alkoxycarbonyl, phenoxycarbonyl, 1-naphthyloxycarbonyl, $C_{2-16}$ carbacyl, $C_{1-20}$ sulfonyl, $C_{1-20}$ sulfamoyl, nitro, fluorinated $C_{1-15}$ alkyl, $C_{1-20}$ sulfinyl, phenyl, 4-chlorophenyl, 4-acetamidophenyl, carboxyl or a salt thereof, and sulfone or a salt thereof;

$R_3$ in Formula (I) is selected from the group consisting of hydrogen, halogen, methyl, propyl, t-butyl, dodecyl, $C_{1-10}$ alkoxy, phenoxy, 2-methylphenoxy, amino, $C_{1-10}$ ureido, $C_{2-30}$ carbamoyloxy, phenyl, 4-tetradecanamidophenyl, 4-bromophenyl, 4-methylthiophenyl, 4-methoxyphenyl, $C_{2-15}$ carbacylamino, carboxyl or a salt thereof, and sulfone or a salt thereof; and $R_4$ in Formula (I) is selected from the group consisting of phenyl, 2pyridyl, 2-benzothiazolyl, and 2-pyrolyl.

3. The dye compound recited in claim 1, wherein X is selected from the group consisting of halogen, fluorinated $C_{1-15}$ alkyl, $C_{1-15}$ alkyl, and $C_{2-16}$ carbacyl.

4. The dye compound recited in claim 2, wherein X is selected from the group consisting of halogen, fluorinated $C_{1-15}$ alkyl, $C_{1-15}$ alkyl, and $C_{2-16}$ carbacyl.

* * * * *

UNITED STATES PATENT AND TRADEMARK OFFICE
CERTIFICATE OF CORRECTION

PATENT NO. : 5,084,571
DATED : January 28, 1992
INVENTOR(S) : Yasuhiro Shimada

It is certified that error appears in the above-identified patent and that said Letters Patent is hereby corrected as shown below:

Column 27, line 8, change "dopdecyloxycarbonyl" to --dodecyloxycarbonyl--
Column 27, line 9, change "-4hydroxyphenoxy" to -- -4-hydroxyphenoxy--
Column 27, line 13, change "oxtyl" to --octyl--
Column 27, line 37, change "-zothiazoluylthio" to --zothiazolylthio--

Column 28, line 10, change "RF$_1$'s" to --R$_1$'s--
Column 28, line 20, change "5dodecyloxy" to --5-dodecyloxy--
Column 28, line 21, change "2-chloro-5-anilino" to --2-chloro-5-[α-(2-t-butyl-4-hydroxyphenoxy)dodecanamido] anilino--
Column 28, line 23, change "-5t" to -- -5-t- --
Column 28, line 27, change "2,4-tert-" to --2,4-di-tert- --
Column 28, line 52, change "C$_{2-30}$" to --C$_{2-20}$--
Column 28, line 58, change "2pyridyl" to --2-pyridyl--

Signed and Sealed this

Ninth Day of November, 1993

Attest:

BRUCE LEHMAN

*Attesting Officer*     *Commissioner of Patents and Trademarks*